United States Patent
Lavallee et al.

(10) Patent No.: US 11,998,283 B2
(45) Date of Patent: Jun. 4, 2024

(54) SYSTEM FOR GUIDING A SURGICAL TOOL RELATIVE TO A TARGET AXIS IN SPINE SURGERY

(71) Applicant: Orthotaxy S.A.S., Gières (FR)

(72) Inventors: Stéphane Lavallee, Saint Martin d'Uriage (FR); Daniel Girardeau-Montaut, Grenoble (FR); Nicolas Demanget, Saint-Egrève (FR)

(73) Assignee: Orthotaxy S.A.S., Gières (FR)

( * ) Notice: Subject to any disclaimer, the term of this patent is extended or adjusted under 35 U.S.C. 154(b) by 727 days.

(21) Appl. No.: 16/493,024

(22) PCT Filed: Mar. 15, 2018

(86) PCT No.: PCT/EP2018/056608
§ 371 (c)(1),
(2) Date: Sep. 11, 2019

(87) PCT Pub. No.: WO2018/167246
PCT Pub. Date: Sep. 20, 2018

(65) Prior Publication Data
US 2020/0008884 A1    Jan. 9, 2020

(30) Foreign Application Priority Data
Mar. 15, 2017   (EP) .................................. 17305281

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 34/30* (2016.02); *A61B 34/70* (2016.02);
(Continued)

(58) Field of Classification Search
CPC ...... A61B 2034/107; A61B 2034/2048; A61B 2034/2051; A61B 2034/2055;
(Continued)

(56) References Cited

U.S. PATENT DOCUMENTS 5,305,203 A    4/1994 Raab
6,470,207 B1   10/2002 Simon et al.
(Continued)

FOREIGN PATENT DOCUMENTS

CN    101448468 A    6/2009
CN    101918855 A    12/2010
(Continued)

OTHER PUBLICATIONS

International Search Report for PCT/EP2018/056608, dated May 3, 2018 (12 pages).
(Continued)

*Primary Examiner* — Michael T Rozanski
(74) *Attorney, Agent, or Firm* — Condo Roccia Koptiw LLP (57) ABSTRACT

The invention relates to a system for guiding a surgical tool (200) held by a user relative to at least one target axis (T) defined in a coordinate system of a patient's spine, comprising: (i) a robotic device (300) comprising: —a base (301), —a guiding device (303) configured for constraining the tool to a guiding axis (G), —a compact motorized actuation unit (304) movable relative to the base (301), coupled to the guiding device (303) for adjusting a position and orientation of said guiding device relative to the target axis, —a support unit (305) connected to the base (301), comprising at least one element designed to make contact with the spine or a region of the patient's body adjacent to the spine so as to provide a partial mechanical link between the guiding device and the spine, (ii) a passive articulated
(Continued)

lockable holding arm (400) supporting the base (301) of the robotic device, (iii) a tracking unit (500) configured to determine in real time the pose of the guiding axis with respect to the coordinate system of the patient's spine, (iv) a control unit configured to: (a) determine the pose of the guiding axis with respect to the target axis, (b) compute a working space of the robotic device for said determined pose, (c) compute at least one indicator representing the capability of the actuation unit to bring the guiding axis in alignment with the target axis based on the computed working space and the pose of the guiding device, (v) a user interface (600) coupled to the control unit, configured for displaying a representation of the guiding axis (G) relative to the target axis (T), wherein the control unit is further configured to control the actuation unit to bring the guiding axis into alignment with the target axis.

20 Claims, 8 Drawing Sheets

(51) Int. Cl.
*A61B 34/30* (2016.01)
*A61B 90/00* (2016.01)
*A61B 90/11* (2016.01)
*A61B 34/10* (2016.01)

(52) U.S. Cl.
CPC .............. *A61B 90/11* (2016.02); *A61B 90/37* (2016.02); *A61B 2034/107* (2016.02); *A61B 2034/2051* (2016.02); *A61B 2034/2055* (2016.02); *A61B 2034/302* (2016.02); *A61B 2090/3762* (2016.02)

(58) Field of Classification Search
CPC ...... A61B 2034/2059; A61B 2034/302; A61B 2090/3762; A61B 34/20; A61B 34/25; A61B 34/30; A61B 34/70; A61B 90/11; A61B 90/37; A61B 90/40; A61B 90/50
See application file for complete search history.

(56) References Cited

U.S. PATENT DOCUMENTS

| | | | |
|---|---|---|---|
| 9,097,756 | B2 | 8/2015 | Piferi |
| 9,125,680 | B2 | 9/2015 | Kostrzewski et al. |
| D749,223 | S | 2/2016 | Vargas et al. |
| 9,308,050 | B2 | 4/2016 | Kostrzewski et al. |
| 9,724,165 | B2 | 8/2017 | Arata et al. |
| 9,877,795 | B2 | 1/2018 | Hao et al. |
| 2002/0038118 | A1 | 3/2002 | Shoham |
| 2007/0093841 | A1 | 4/2007 | Hoogland |
| 2010/0041985 | A1* | 2/2010 | Simon .................... A61B 6/463 378/62 |
| 2013/0303883 | A1 | 11/2013 | Zehavi et al. |
| 2014/0039307 | A1 | 2/2014 | Harhen |
| 2014/0337773 | A1 | 11/2014 | Phang et al. |
| 2015/0202009 | A1 | 7/2015 | Nussbaumer et al. |
| 2015/0223897 | A1 | 8/2015 | Kostrzewski et al. |
| 2015/0305817 | A1 | 10/2015 | Kostrzewski |
| 2015/0366624 | A1 | 12/2015 | Kostrzewski et al. |
| 2016/0008011 | A1 | 1/2016 | Kostrzewski |
| 2016/0038238 | A1 | 2/2016 | Kostrzewski et al. |
| 2016/0081753 | A1 | 3/2016 | Kostrzewski |
| 2016/0081754 | A1 | 3/2016 | Kostrzewski et al. |
| 2016/0113720 | A1 | 4/2016 | Lavallee et al. |
| 2016/0128789 | A1 | 5/2016 | Kostrzewski et al. |
| 2016/0135816 | A1 | 5/2016 | Lavallee et al. |
| 2016/0235492 | A1 | 8/2016 | Morard et al. |
| 2017/0007334 | A1 | 1/2017 | Crawford et al. |
| 2017/0056116 | A1 | 3/2017 | Kostrzewski |
| 2017/0209218 | A1 | 7/2017 | Sahay et al. |

FOREIGN PATENT DOCUMENTS

| | | |
|---|---|---|
| CN | 103607958 A | 2/2014 |
| CN | 104688341 A | 6/2015 |
| CN | 105191327 A | 12/2015 |
| CN | 105431102 A | 3/2016 |
| CN | 106132330 A | 11/2016 |
| CN | 106413621 A | 2/2017 |
| EP | 0326768 A2 | 8/1989 |
| EP | 1414362 A1 | 5/2004 |
| EP | 1571581 A1 | 9/2005 |
| EP | 2356940 A1 | 8/2011 |
| JP | H01 280449 A | 11/1989 |
| JP | 2016523614 A | 8/2016 |
| JP | 2017-012457 A | 1/2017 |
| KR | 20150138520 A | 12/2015 |
| KR | 101633774 B1 | 6/2016 |
| WO | 2012/131660 A1 | 10/2012 |
| WO | 2015183046 A | 1/2015 |
| WO | 2015/115807 A1 | 8/2015 |
| WO | 2015/115809 A1 | 8/2015 |

OTHER PUBLICATIONS

Ortmaier T et al., "A hands-on-robot for accurate placement of pedicle screws," 2006 IEEE International Conference on Robotics and Automation (ICRA): Orlando, Florida, May 15-19, 2006, IEEE Operations Center, Piscataway, NJ, May 15, 2006, pp. 4179-4186, XP010921907, DOI: 10.1109/ROBOT.2006.1642345, ISBN: 978-0-7803-9505-3, the whole document (8 pages).

* cited by examiner

SYSTEM FOR GUIDING A SURGICAL TOOL RELATIVE TO A TARGET AXIS IN SPINE SURGERY

CROSS-REFERENCE TO RELATED APPLICATIONS

This application is a national stage application of International Application No. PCT/EP2018/056608, filed on Mar. 15, 2018. International Application No. PCT/EP2018/056608 claims priority to and the benefit of European Application No. 17305281.2, filed Mar. 15, 2017. The entire contents of each of these applications are incorporated herein by reference.

FIELD OF THE INVENTION

The invention relates to a system for guiding a surgical tool held by a user relative to at least one target axis defined in a coordinate system of a patient's spine.

BACKGROUND OF THE INVENTION

Spine surgery generally involves implanting a screw in the pedicles of a patient's vertebrae.

Due to the small size of the pedicles, each screw has to be positioned and oriented accurately relative to a target axis that passes substantially though the center of the pedicle. Each target axis is usually planned preoperatively or intraoperatively, based on a 3D medical image of the patient's spine. It is assumed that each target axis is planned in a 3D image acquired during surgery and referenced with respect to a patient's coordinate system attached to a reference tracker.

Since screws have to be implanted in the pedicles of several (at least two) vertebrae, the surgical intervention is time-consuming and repetitive.

In order to reduce the duration and to increase the accuracy of the surgery, it is desirable to provide a robotic system that supports a guiding device at its working end, in order to assist positioning and implantation of the screws through the guiding device.

To that end, some applications have been developed using large robots, for example the ROSA robot, from Zimmer Inc.

In robotics systems for spine, several axes are planned and known in the coordinate system of the reference tracker, the robot is equipped with a tracker at its tip and the robot is moved and servoed to the target axes, consecutively. Usually four, six or eight screws are placed and they are used to fix bars between the screw heads to prevent spine instability.

However, for several reasons, such large robots are not convenient for placing a screw in a pedicle. First, these robots are very cumbersome and hinder the work of the surgeon's assistant—who may remain at a distance from the surgeon due to the presence of the large robot, thus rendering the handling of the surgical tools complicated.

Secondly, the perfect stiffness of a long kinematic chain is difficult to achieve and requires expensive machining of the robot components. However, for maintaining a perfect accuracy, it is important to make sure that once in the correct position and orientation, the guiding device held by the robot does not move in order not to deviate the position and/or orientation of the surgical tool relative to the target axis.

In addition, such robots are quite slow and hardly comply with quick motion that may occur during the use of the surgical tools in order to be servoed to the reference tracker motions. For example, when a tool is introduced in a guide held by a robot, it pushes the vertebra when it comes to contact it, which can be quite sudden.

In general, maintaining accuracy (in programming and not just repeatability) and speed for large robots is a technical challenge.

At last, since the robot knows only the part of its environment that has previously being modelled (which is not its complete environment), there exists a risk of collision of the robot with its environment (e.g. the patient, wires, a tracker attached to the patient or any other tool in the vicinity of the patient, imaging devices) when the robot moves from its rest position to a target axis.

On the other hand, compact, bone-mounted robots have been developed.

In particular, patent EP1414362 describes a system comprising a robotic device which is attached to a patient's vertebra by a clamp. However, despite its compactness, such a bone-mounted robot presents the drawback that its weight may break the vertebra. In addition, the range of motion of the working end of the robot is limited. Thus, if the robot is not attached in a position compatible with an alignment of the guiding device with the target axis, the surgeon has either to remove the robot and re-attach it in a more suitable position, or to use an adapter.

None of these solutions, which render the surgical intervention very tedious, is convenient for the surgeon.

SUMMARY OF THE INVENTION

A goal of the invention is to design a robotic system for spine surgery, which avoids the above drawbacks.

To that end, the invention provides a robotic system for guiding a surgical tool held by a user relative to at least one target axis defined in a coordinate system of a patient's spine, comprising:
(i) a robotic device comprising:
a base,
a guiding device configured for constraining the tool to a guiding axis while the tool is being manipulated by the user,
a compact motorized actuation unit movable relative to the base, coupled to the guiding device for adjusting a position and orientation of said guiding device relative to the target axis,
a support unit connected to the base, comprising at least one element designed to make contact with the spine or a region of the patient's body adjacent to the spine so as to provide a partial mechanical link between the guiding device and the spine,
(ii) a passive articulated lockable holding arm supporting the base of the robotic device,
(iii) a tracking unit configured to determine in real time the pose of the guiding axis with respect to the coordinate system of the patient's spine,
(iv) a control unit configured to:
(a) determine the pose of the guiding axis with respect to the target axis,
(b) compute a working space of the robotic device for said determined pose,
(c) compute at least one indicator representing the capability of the actuation unit to bring the guiding axis in alignment with the target axis based on the computed working space and the pose of the guiding device,
(v) a user interface coupled to the control unit, configured for displaying a representation of the guiding axis relative to the target axis, wherein the control unit is further configured to control the actuation unit to bring the guiding axis into alignment with the target axis.

In the present text, the term "spine" designates a set of vertebrae. This term thus includes one or several vertebrae, or even the whole spine.

In the present text, a compact mechanism is a mechanism that has maximal dimensions of about forty centimeters in all dimensions, and preferably ten to twenty centimeters in length and a width of seven to fifteen centimeters. The length of the mechanism is defined as the dimension in the direction of the guiding axis and the width is the dimension in the two other directions.

By "partial mechanical link" is meant a mechanical link between at least two parts, wherein a relative movement of said at least two parts in at least one degree of freedom is possible. This term excludes a "complete" mechanical link, i.e. a link wherein no relative movement between the parts is allowed. An example of such complete mechanical link would be rigidly attaching the robotic system to a bone to be cut by at least one screw or pin implanted into said bone.

As described in further detail below, said partial mechanical link provided between the guiding device and the patient's spine may be direct, meaning that the support unit is in contact with the anatomical structure (vertebra) to be treated itself, or indirect, meaning that the support unit is in contact with a part of the patient's body adjacent to the anatomical structure to be treated. Said adjacent part may consist of a vertebra adjacent to the vertebra to be treated, or a vertebra located a few levels above or below, or of soft tissues (possibly including the skin) that surround said vertebra, or the pelvis bone, or the cranium for cervical vertebrae, or a frame attached to the cranium. An indirect partial mechanical link may also be obtained when the support unit is held by a user's hand and that said hand leans onto the vertebra or the soft tissues and skin surrounding the vertebra to be treated.

The system is able to compensate for a given amount of pose errors (e.g. due to small movements of the user or involuntary movement of the patient).

By "pose" is meant, in the present text, the 3D position and 3D orientation of the guiding device in up to six degrees of freedom. It is to be noted that in this application, it is not necessary to determine all six degrees of freedom but only some of them. In particular, the guiding device is moved according to at least four degrees of freedom.

By "alignment" of the guiding axis with a target axis, is meant in the present text that said guiding axis deviates from the target axis by a distance of less than 0.5 mm and an angle of less than 0.5°. Preferably, the guiding axis coincides perfectly with the target axis.

While the partial mechanical link allows slight movements of the robotic device relatively to the anatomical structure (due to the insertion of the tool in the anatomical structure, the movement of the user holding the tool, involuntary movement of the patient, or vibrations during the tool operation), the actuation unit allows taking into account these slight movements to adjust the position of the guiding axis in real time so as to maintain its alignment with the target axis. Real time means with a frame rate of at least twenty Hertz (ideally three hundred Hertz), and a lag less than fifty milliseconds (ideally five milliseconds)

According to a preferred embodiment, the capability of the actuation unit to bring the guiding axis in alignment with the target axis is computed based on a distance between an envelope of the working space and the target axis.

Advantageously, said capability is at a first level when the target axis is within the working space, with a distance between the envelope of the working space and the target axis below a determined threshold, and at a second level when the target axis is within the working space, with a distance between the envelope of the working space and the target axis greater than said determined threshold.

According to an embodiment, the actuation unit is configured to be activated only when the capability of the actuation unit to bring the guiding device into alignment with the target axis is at the second level.

According to an embodiment, the user interface is configured to display a 2D representation of the guiding axis relative to the target axis, wherein said 2D representation comprises, in a plane perpendicular to the target axis: a first circle having a center representing a distal point of the guiding axis, a second circle having a center representing a proximal point of the guiding axis, and a cross having an intersection representing the target axis.

Alternatively, the user interface may be configured to display a 3D representation of the guiding axis relative to the target axis, wherein said 3D representation comprises: a first cross having an intersection representing a distal point of the target axis, a second cross having an intersection representing a proximal point of the target axis, and a bar representing the guiding axis.

According to an embodiment, the user interface is further configured to display said at least one computed indicator representing the capability of the actuation unit to bring the guiding axis in alignment with the target axis.

Said computed indicator may be displayed on the user interface as an element having at least one feature variable as a function a distance between the envelope of the working space and the target axis.

In particular, said computed indicator may be displayed on the user interface as a three-dimensional view comprising a pair of distal and proximal tori representing respectively the envelope of the working space in a distal and a proximal section of the guiding device, the user interface further displaying the guiding axis relative to said distal and proximal tori.

Alternatively, said computed indicator may be displayed on the user interface as a distal torus and a proximal disc representing respectively the envelope of the working space in a distal section of the guiding device and on a reference surface, the user interface further displaying the guiding axis relative to said distal torus and proximal disc, wherein the reference surface is selected from: the patient's skin, an entry point of the tool in the spine, and a section of the spine passing through a target point within the spine.

According to another embodiment, said computed indicator may be displayed on the user interface as a distal torus and a proximal disc representing respectively the envelope of the working space in a distal section of the guiding device and on a section of the spine comprising a target point, the user interface further displaying the guiding axis relative to said distal torus and proximal disc, wherein the disc contains a slice of a 3D medical image passing through said target point.

Advantageously, the control unit may be configured to select, among several target axes, the target axis closest to the current position of the robotic device, and to carry out steps (a) to (c) for said selected target axis.

According to an embodiment, the actuation unit is configured to be activated only when the holding arm is locked.

According to an embodiment, the control unit is configured to, once the guiding device has been aligned with a first target axis and the holding arm has been unlocked, select a second target axis closest to the first axis.

According to an embodiment, the robotic device comprises a trigger configured to simultaneously lock the holding arm and activate the actuation unit to bring the guiding device into alignment with the target axis.

According to an embodiment, the actuation unit comprises two five-bar linkages configured to move in parallel planes.

According to an embodiment, the guiding device is a tube.

According to an embodiment, the tracking unit comprises a first optical tracker attached to the guiding device and a second optical tracker configured to be attached to the patient's spine.

Alternatively, the tracking unit may comprise an electromagnetic emitter attached to the guiding device and an electromagnetic sensor configured to be attached to the patient's spine.

BRIEF DESCRIPTION OF THE FIGURES

Further features and advantages of the invention will appear in the following detailed description, with reference to the appended drawings, wherein.

DETAILED DESCRIPTION OF EMBODIMENTS OF THE INVENTION

As will be explained in further detail below, the system is used in a context in which at least one target axis along which the anatomical structure has to be treated is planned before performing the treatment with the tool. The treatment generally includes drilling a bore into the anatomical structure and/or fixing a screw into the anatomical structure.

In spine surgery, it is usually required to fix pedicular screws into several vertebrae, on both sides of the spine. Thus, the placement of each screw is associated with a target axis passing through the respective pedicle. The system according to the invention allows placing the screws successively in the required vertebra within a short time and requiring only minimal actions from the user.

Planning of such a target axis is performed using pre-operative images (e.g. CT, MRI, Ultrasound images, 2D or 3D X-rays in combination with statistical shape models, PET, etc.) or intra-operative 3D data (e.g. intra-operative CT or CBCT (Cone Beam Computed Tomography), intra-operative MRI, Ultrasound images, 2D or 3D intra-operative X-ray images, geometric data provided by localizing systems and providing 3D points, clouds of 3D points, surfaces reconstructed from clouds of 3D points, etc.), or both. In the following description, it is considered that 3D intra-operative images are acquired using a CBCT Multiple computer-assisted surgery methods are used to register the target axis with a reference coordinate system attached to the anatomical structure to be operated.

Typically, intra-operative images or data are used to register pre-operative images in a unique coordinate system attached to the anatomical structure, and usually represented by a tracker that can use any of computer assisted surgery technologies (optical tracker made of reflective markers, optical tracker made of active LEDs, electromagnetic trackers made of coils, combination of inertial sensors, etc.).

Using any of these conventional computer-assisted surgery methods results in that the target axis has a known geometric representation in a coordinate system attached to the anatomical structure to be operated, and whose movements are tracked in real-time by a tracking unit as it will be detailed below.

Figure 1:
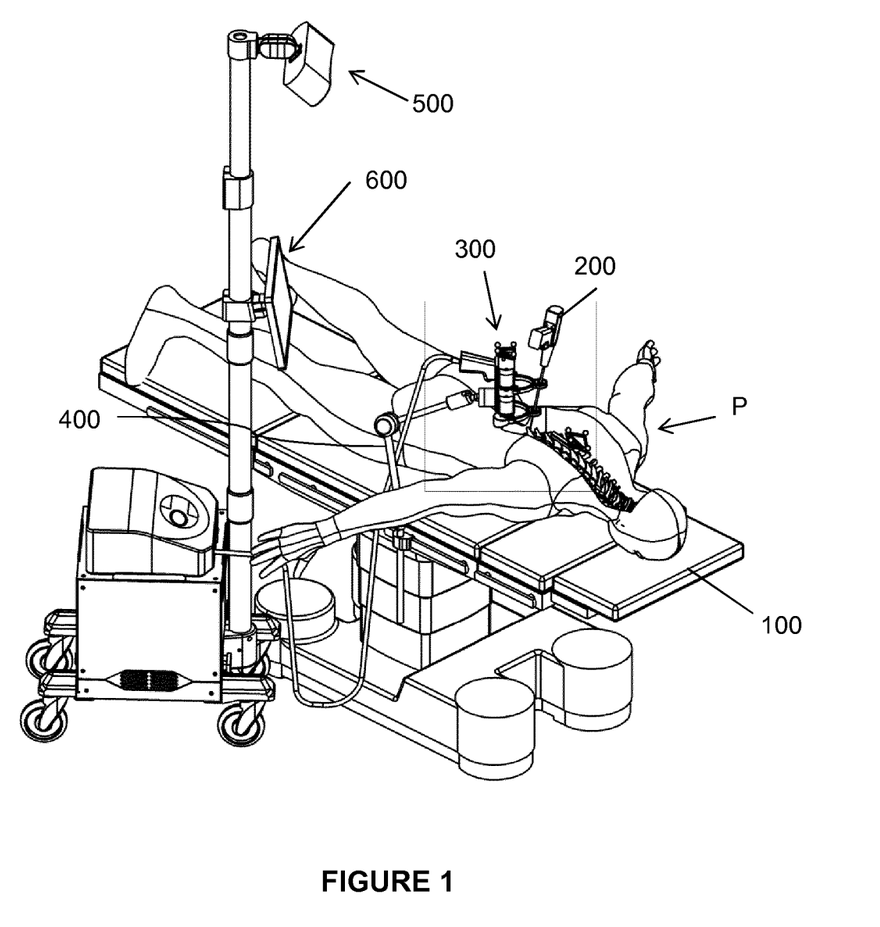
FIG. 1 shows an overview of a surgical system according to the invention

FIG. 1 shows an overview of a surgical system according to the invention.

The system may be used either in minimally invasive surgery, where only a small incision is made into the soft tissues for each vertebra to be treated, or in open surgery.

The patient P is lying on an operating table 100, generally in the prone position.

A surgical tool 200 which is intended to drill a bore or to attach a screw along at least one target axis is used by a user (not shown) such as a surgeon. Said tool may be a drill, a trocar, a squared awl, a screwdriver, a burr, or any other tool that has to be guided along a determined axis.

Figure 3:
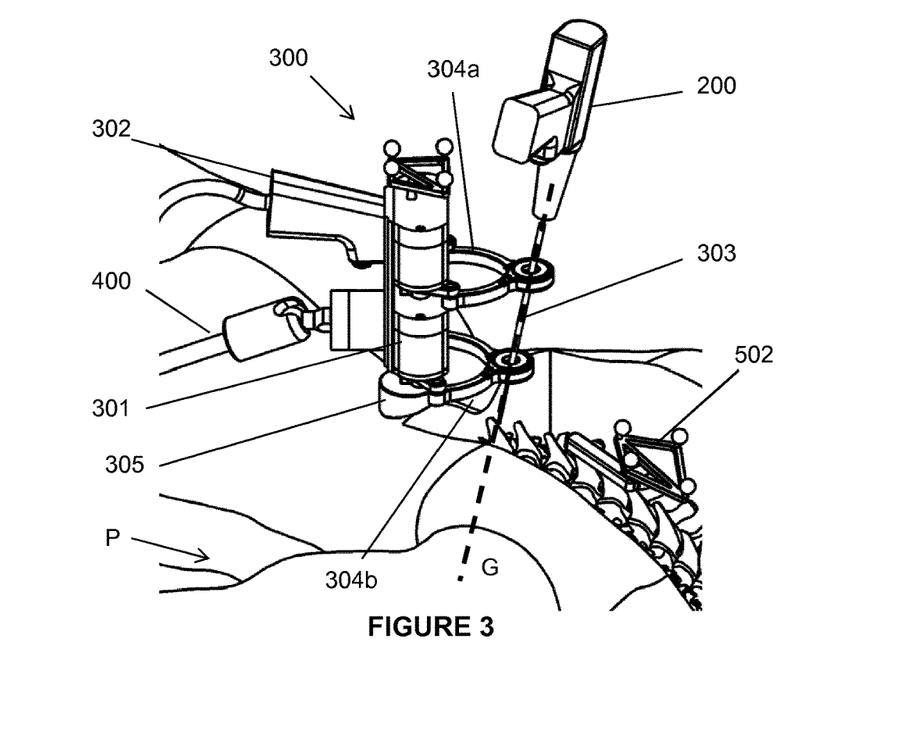

A robotic device 300 is used to guide movement of the surgical tool along a guiding axis G (shown in FIG. 3).

The robotic device 300 comprises a base 301 by which the robotic device can be manipulated. To that end, the base may comprise a handle 302.

The robotic device 300 further comprises a guiding device 303 that defines the guiding axis G.

The guiding device 303 is connected to the base 301 by an actuation unit 304 that allows adjusting position and orientation of the guiding device in at least four degrees of freedom.

The guiding device 303 is typically a tube, with a cross section—which is generally circular—adapted to the tool size. In such case, the tool 200 can be manually inserted through the tube by the surgeon in order to perform the surgical intervention. The tool is thus not attached to the guiding device and is manipulated by the user separately from the robotic device.

The guiding device may comprise an additional degree of freedom consisting of a translation along the guiding axis. For example, the guiding device may comprise a slide to which the tool can be directly attached (not shown). Said slide may be motorized.

The actuation unit 304 is any compact mechanism that can position a line segment in space. It can have a serial architecture like a compact anthropomorphic arm or any parallel architecture like a hexapod for example, or a combination of serial and parallel parts.

According to a preferred embodiment (better seen in FIG. 3), the actuation unit 304 comprises two five-bar linkages 304a, 304b movable in two parallel planes, a first one (304a) being coupled to a distal portion of the guiding device and a second one (304b) being coupled to a proximal portion of the guiding device 303. In the present text, "distal" and "proximal" designate parts that are respectively farther and closer to the patient.

The actuation unit 304 is moved by actuators, each actuator having encoders, such that the pose of the guiding device is known relative to the base. A working space of the robotic device is thus defined as the volume comprising all the positions of the guiding device reachable by the actuation unit when the base is held in a given position.

Besides, the robotic device 300 comprises a support unit 305 coupled to the base 301 and configured to create a partial mechanical link between the guiding device 303 and the patient's spine S.

The support unit 300 may be configured to bear onto the patient's skin. To that end, the support unit may comprise a soft cushion. It can be also a detachable sticker, a vacuum mechanism, a deformable shape that can be quickly adapted to the patient's skin surface (this list not being limitative). The support unit can be also reinforced by using masses that increase its stability. For example, it can be a deformable pad made of a heavy material.

Otherwise, in particular in case of open surgery, the support unit may be configured to bear on a vertebra. To that end, the support unit may comprise a pin, two pins, a hook, a clip, a staple, or a V-shaped end intended to directly engage a vertebra.

The support unit can be adjusted in several positions with respect to the robot base, continuously or using discrete positions. For example, a linear bar slides in the robot base and contains the support unit at its extremity and the sliding can be locked by a button with a spring or a screw.

The system further comprises a passive articulated lockable holding arm 400 supporting the base 301 of the robotic device 300.

The holding arm 400 is mounted on a mechanical support such as rails attached to the operating table 100. To improve stability of the holding arm, the two rails along the table can be attached to each other using a mechanism below the table to create a bridge between the rails. Alternatively, the holding arm can be also mounted on a mobile cart, placed on the side of the operating table.

The holding arm 400 is articulated with several degrees of freedom and comprises a switch to lock its position. The switch can be one button or two buttons for safety purpose. It can be also a footswitch. The holding arm may use any suitable technology (e.g. pneumatic arms, hydraulic arms, piezo-electric arms, mechanical arms, arms with brakes, etc.).

The holding arm 400 allows supporting the weight of the robotic device 300 and maintaining the base and the support unit in a fixed position when the guiding device is aligned with the target axis.

The system also comprises a tracking unit 500, such that the pose of the guiding device 303 and the spine is tracked in real-time and is shared between a real time control unit and a planning system.

At least one coordinate system 501 is attached to the spine while at least one coordinate system 502 is attached to the guiding device 303.

The tracking unit 500 measures the relative motions between both coordinate systems 501, 502 in real time.

The data obtained by the tracking unit are transferred to the control unit via any suitable connection, with wires or wireless.

The system also comprises a user interface 600 coupled to the control unit that is intended to display feedback information to a user and enable system configuration by the user. The feedback information comprises at least a representation of the guiding axis relative to the target axis.

Said user interface 600 may advantageously comprise a screen located on the same cart 700 as the control unit and tracking unit.

In addition to or instead of said screen, the user interface may comprise an indicator that is arranged on the robotic device itself to provide information to the user.

A surgical system wherein the control unit, tracking unit and/or user interface are embedded in the robotic device itself would still be within the scope of the invention, provided that the embedded units are powered by a sufficiently powerful battery and that their size and weight do not hinder the manipulation of the robotic device by the user. For example, micro cameras can be attached to the base of the robotic device and markers can be attached to the spine and to the guiding device.

The control unit typically comprises power supply, AC/DC converters, motion controllers to power the AC/DC motors of the actuation unit, fuses, real-time control system interface circuits.

The control unit is able to carry out the proposed real time control algorithms at a reasonably high frequency with small lag.

The control unit computes in real time the pose of the guiding device with respect to a selected target axis based on the data provided by the tracking unit.

The control unit and tracking unit may be arranged in a cart that can be moved in the operating room. They can be also mounted on separate carts, articulated holding arms, lighting systems, or the tracking unit can be also mounted directly on the anatomical structure or on some parts attached to the robotic device. For example, the guiding device can support rigidly an electromagnetic emitter and electromagnetic sensors can be attached to the anatomical structure.

The control unit is configured to:

(a) determine the pose of the guiding axis with respect to the target axis; this determination can be made since the pose of the target axis relative to the patient's coordinate system is known.

(b) compute a working space of the robotic device for said determined pose; this computation may involve the following steps: the knowledge of the positions of the actuators of the actuation unit allows determining the pose of the base relative to the patient's coordinate system, then, the working space is determined for said pose of the base, using the maximum displacements allowed by each actuator of the actuation unit, (c) compute at least one indicator representing the capability of the actuation unit to bring the guiding axis in alignment with the target axis based on the computed working space and the pose of the guiding device;

(d) provide to the user interface the pose of the guiding axis relative to the target axis, which is displayed by the user interface;

(e) control the actuation unit to bring the guiding axis into alignment with the target axis.

According to an embodiment, the computed indicator may be used by the control unit to activate or not the actuation unit, without being necessarily displayed to the user.

According to a preferred embodiment, the computed indicator is provided by the control unit to the user interface so as to be displayed (examples of such an indicator will be described below with reference to FIGS. 6-10).

This computed indicator is useful because, if the target axis is not contained in the working space, the actuation unit will not be able to bring the guiding device in alignment with the target axis. On the other hand, the fact that the target axis is contained in the working space may not be sufficient to ensure a satisfactory working of the robotic device. Indeed, if the target axis is too close to the envelope (outer surface) of the working space, the actuation unit will be able to align the guiding device with the target axis but there exists the risk that, in case of a relative small movement of the patient and the guiding device resulting of the target axis extending out of the working space, the actuation unit is not able to maintain this alignment. Thus, for a proper operation of the system, it is preferable to ensure a certain distance (also called compensation margin) between the envelope of the working space and the target axis.

In other words, the capability of the actuation unit to bring the guiding axis in alignment with the target axis may be at two different levels:
- a first level (low level) when the target axis is within the working space, with a distance between the envelope of the working space and the target axis below a determined threshold, and
- a second level (high level) when the target axis is within the working space, with a distance between the envelope of the working space and the target axis greater than said determined threshold.

Preferably, the actuation unit is activated only when its capability to bring the guiding axis in alignment with the target axis is at the second level, and not at the first level, in order to ensure that the actuation unit will be able to compensate a possible movement of the guiding device relative to the target axis during operation of the tool so as to always maintain alignment of the guiding axis with the target axis.

In addition, the user interface may provide indications to the user on how to position the robotic device appropriately when the working space does not contain the target axis. For example, round arrows can appear to indicate to the user to turn the robot in one direction before locking the holding arm and straight arrows can indicate the need for a translation. Such arrows can be on the screen of the user interface or directly on the robotic device itself, for example using a small display or LEDs.

Embodiments of the operation of the system will be described below.

Before using the robotic device, a user plans the intervention on the planning system, based on pre-operative and/or intra-operative medical images and data.

This planning step allows determining a target axis suited to perform the treatment of each vertebra (generally, one target axis for each of the two pedicles of each vertebra).

The planning system may form part of the surgical system according to the invention; otherwise, the planning system may be provided separately and connected to the control unit.

During the surgical intervention, the user may either use preoperative data/images together with intra-operative registration methods, or use directly intraoperative data/images.

In both cases, the result of the planning consists of at least one target axis, the pose of each axis being determined in the coordinate system of the reference patient's spine.

The pose of each target axis is then transferred to the control unit.

The control unit initializes its sub-systems and the robotic device is ready to use.

During the surgical intervention, in a first step (approach step) the user releases the button(s) of the holding arm, moves the base of the robotic device which is held by the holding arm so as to bring the base in a position in which the actuation unit is able to bring the guiding device in alignment with the target axis, and connects the support unit to the spine or an adjacent region of the patient's body to provide a partial mechanical link between the guiding device and the spine. When a suitable pose of the base has been reached, the user releases the buttons of the holding arm, and locks the holding arm so as to immobilize the base. The user can then release totally the base in order to manipulate the surgical tool since the holding arm is holding the actuation unit.

In this approach step, the robotic device is preferably inactive, the guiding device being maintained in a neutral position of the actuation device. Then, in a second step (operative step), after the holding arm has been locked, the actuation unit is activated to align the guiding device with the target axis. The activation of the control unit can be launched automatically as soon as the user releases the button(s) of the holding arm.

Alternatively, the actuation unit of the robotic device could be continuously activated during the approach step, the guiding device being servoed to the target axis. The user locks the holding arm once the guiding device is aligned with the target axis.

In a third step, the user uses the surgical tool which is guided by the guiding device. The guiding device remains servoed to the target axis until the holding arm is unlocked.

According to a preferred embodiment, the switch used to lock the holding arm is also configured to activate the actuation unit. For example, the switch may comprise a trigger which is pressed by the user when displacing the base of the robotic device. To that end, the trigger may be arranged on the handle of the base. When the robotic device is in a suitable position for aligning the guiding device with the target axis, the user releases the trigger, which activates the actuation unit to move the guiding device to the target axis.

In this way, the operation of the system is very simple and straightforward, minimizing the actions to be made by the user.

The system according to the invention is particularly advantageous when the guiding device has to be aligned successively with several target axes.

Indeed, the control unit is able to detect, among a plurality of target axes to be reached, the one closest to the current position of the robotic device, and carries out the above steps for said selected target axis. Then, once the holding arm has been unlocked and a new target axis has to be reached, the control unit selects the next target axis closest to the current position of the robotic device. However, the user can always press a button on the user interface to force the robotic device to reach a predefined target axis and not the closest one.

The system can thus be used as a gun, i.e. involving only an action of the trigger to lock/unlock the holding arm and activate/deactivate the actuation unit, for each target axis to be reached.

Figure 2:
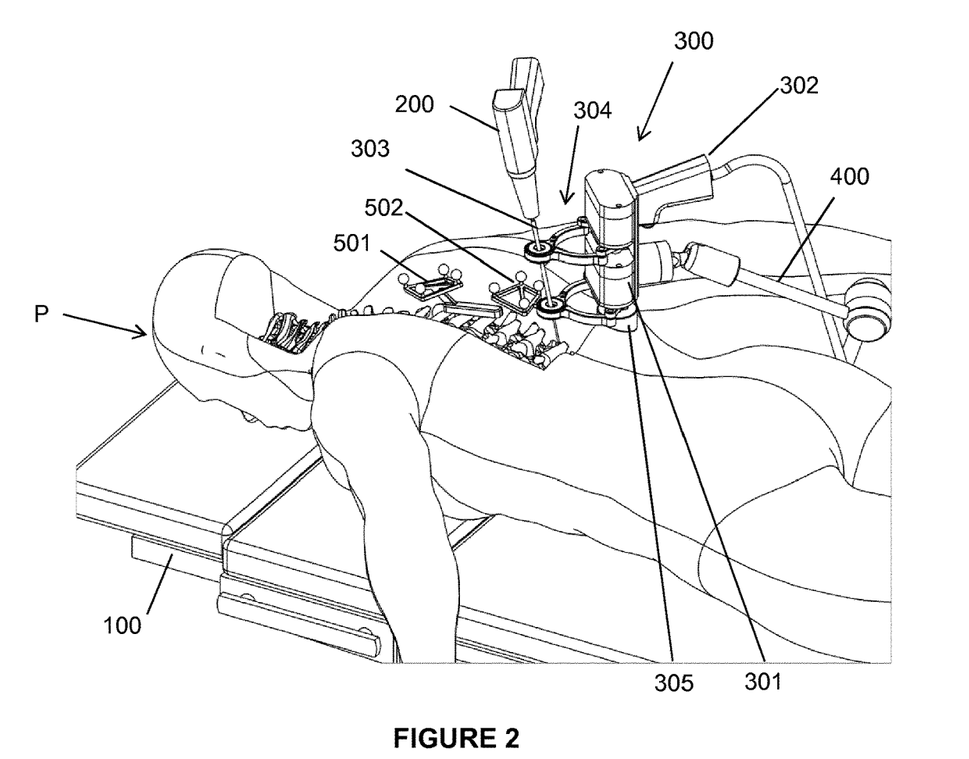
FIGS. 2 and 3 show perspective views of a system according to an embodiment of the invention, based on optical tracking.

FIGS. 2 and 3 show perspective views of a robotic device of a system according to an embodiment of the invention (the control unit and user interface are not shown in these figures).

In this embodiment, the tracking is based on optical technology. An advantage of this technology is that it is not affected by the presence of metal tools in the operative environment.

The robotic device comprises a base that comprises a handle for manipulation of the robotic device. The base is further attached at the end of a holding arm.

The robotic device comprises a guiding device and an actuation unit connecting the guiding device to the base. In the illustrated embodiment, the guiding device is a linear tube with a circular cross section.

In the illustrated embodiment, the actuation unit comprises a first five-bar linkage connected to a distal section of the guiding device by a first ball joint, and a second five-bar linkage connected to a proximal section of the guiding device by a second ball joint. The five-bar linkages move in two parallel planes. The guiding device may be fixed to at least one of the ball joints, and may slide relative to the other one.

However, the architecture of the robotic device is not limited to the illustrated architecture. Any other compact robotic architecture with three, four, five or six degrees of freedom could be used. For example, the robotic device could have an anthropomorphic architecture made of six rotoid joints.

In any case, the architecture of the robotic device is compact, with a short kinematic chain, ensuring that it can be actuated in a very fast way so as to compensate any deviation of the guiding axis relative to the target axis, and still remain very accurate.

The handle of the robotic device advantageously comprises a trigger configured to lock or unlock the holding arm, and to simultaneously activate or deactivate the actuation unit.

A first optical tracker 502 is attached to the guiding device. From this tracker position it is possible to compute the position of the robot base. It is also possible to use a tracker on the robot base, or two trackers, one on the base, one on the guiding device for redundancy and safety purpose.

A second optical tracker 501 is attached to a patient's vertebra and defines a coordinate system of the patient.

Both trackers are arranged in the field of view of a 3D camera (not shown) such as Polaris Spectra or Vicra camera (Northern Digital Inc., Canada) or faster generations.

The tracking system allows determining in real time the position and orientation of the guiding device relative to the patient's coordinate system.

Since the motors of the actuation unit 304 have a known position relative to the base, the control unit is able to compute the position and orientation of the base relative to the coordinate system of the patient. The control unit is also able to compute the working space of the robotic device for each pose of the base.

Figure 4:
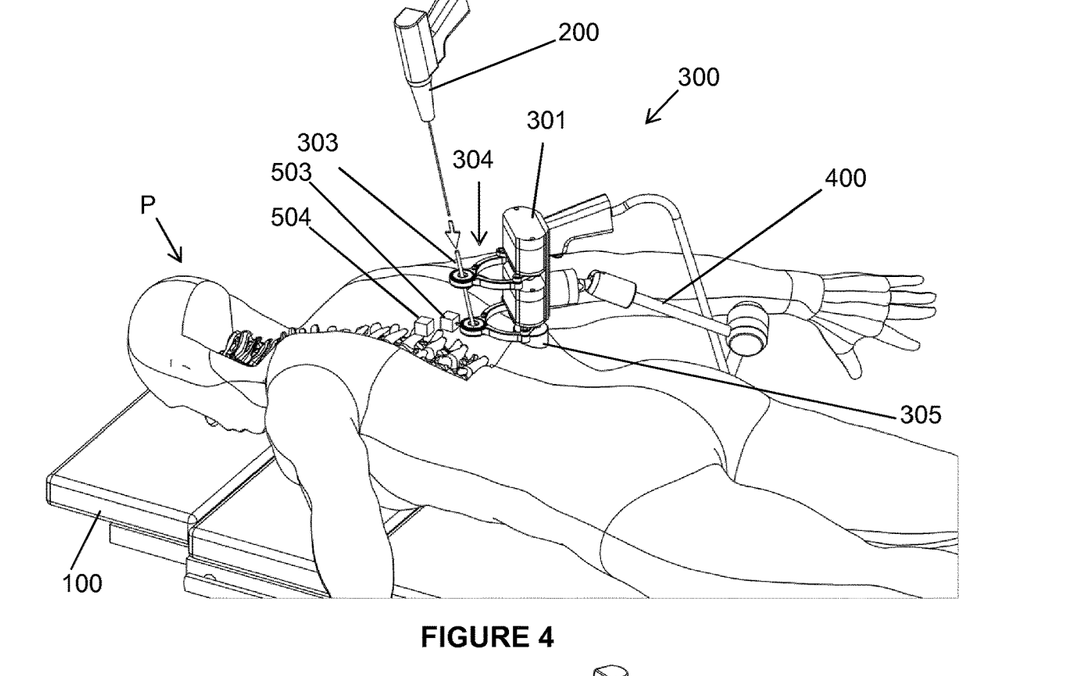
FIGS. 4 and 5 show perspective views of a system according to an embodiment of the invention, based on electromagnetic tracking.
Figure 5:
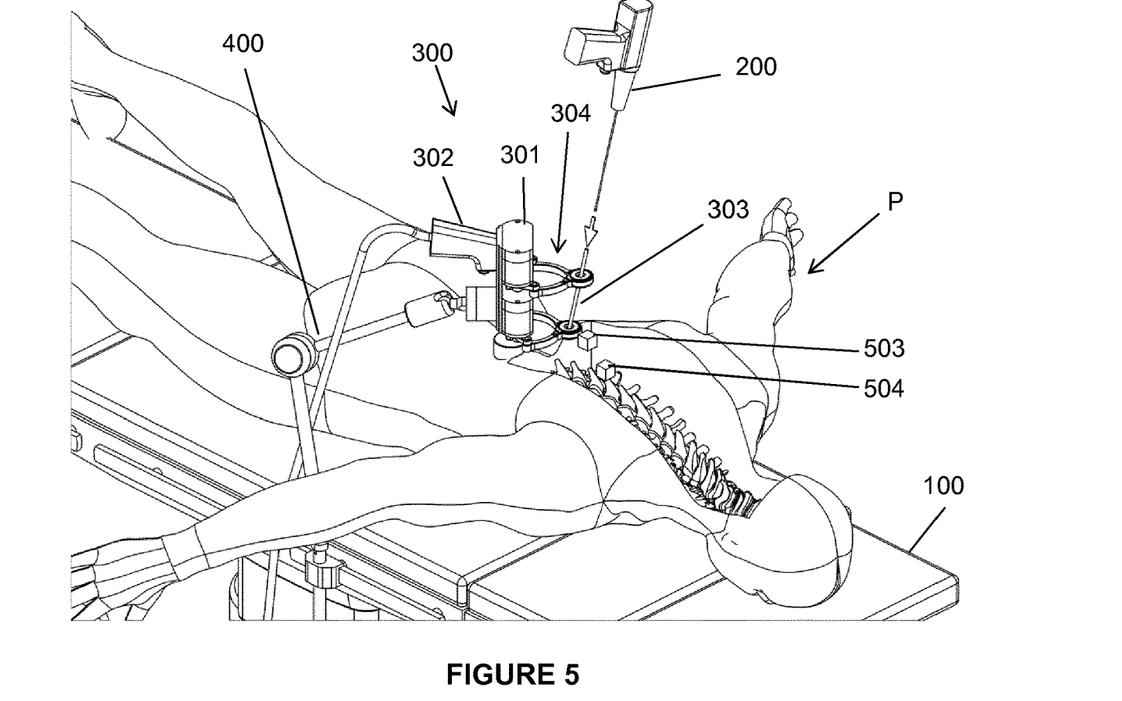

FIGS. 4 and 5 show perspective views of a robotic device of a system according to another embodiment of the invention (the control unit and user interface are not shown in these figures).

The architecture of the robotic device is similar to the one described with reference to FIGS. 2-3 and will thus not be described again.

In this embodiment, the tracking is based on electromagnetic technology. An advantage of this technology is that the trackers are very compact and thus suitable for minimally invasive surgery and that they avoid the line-of-sight issues.

In a preferred embodiment, the emitter 503 is attached to the proximal portion of the guiding device 303. Alternatively, the emitter could be attached to the proximal portion of the base 301.

A sensor 504 is attached to a patient's vertebra and defines a coordinate system of the patient.

Although electromagnetic trackers are sensitive to metal objects that generate artefacts, this arrangement ensures that the emitter 503 and sensor 504 are very close to each other, without any metal object between them. Mechanisms to check the presence of metal artefacts can be used to ensure that the measures are accurate.

FIGS. 6 to 10 show various but not limitative embodiments of the views that may be displayed by the user interface in order to show the position of the guiding device relative to the target axis and to present at least one indicator of the capability of the actuation unit to align the guiding device with the target axis. Said views may be either two-dimensional (2D) or three-dimensional (3D).

Figure 6:
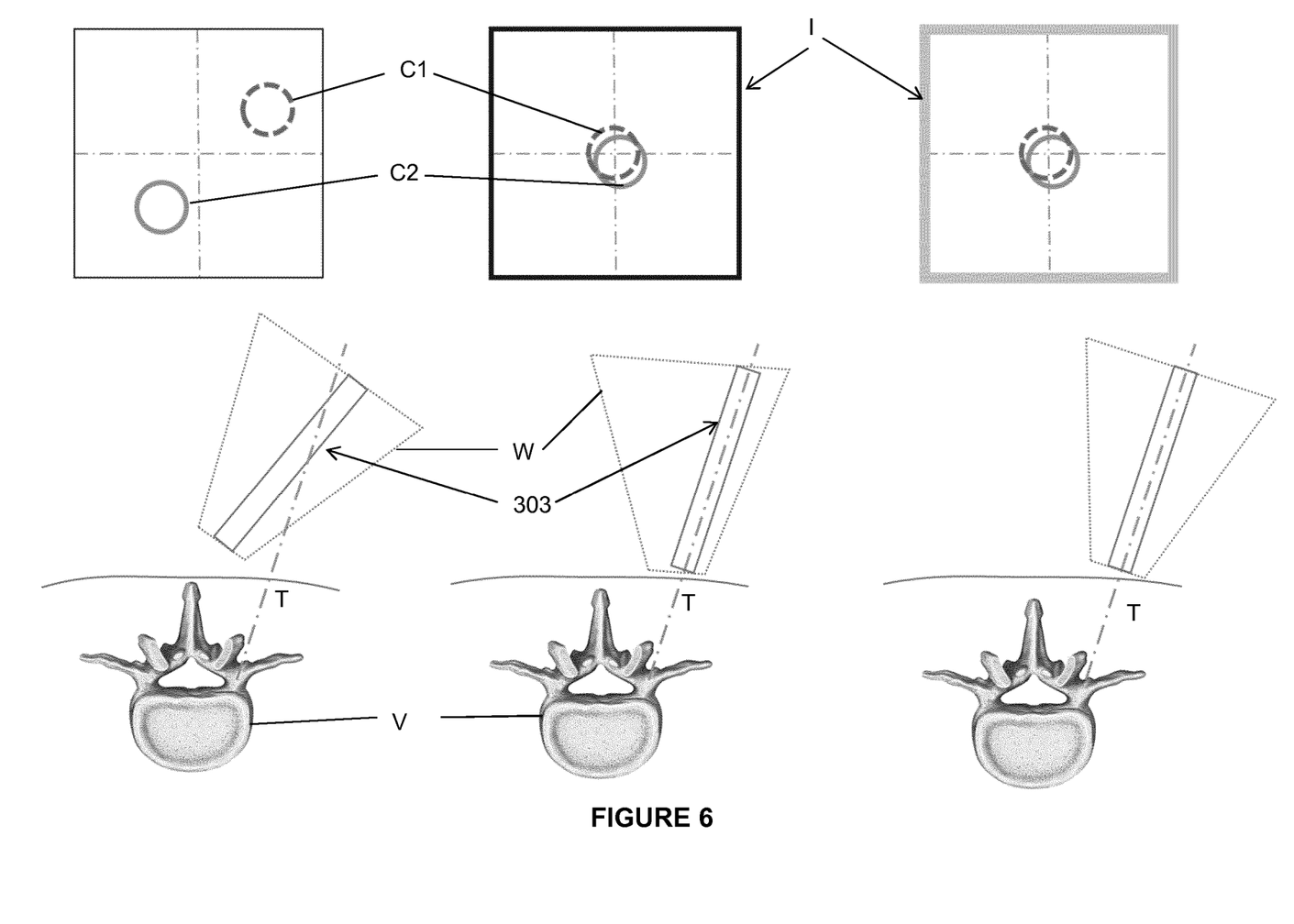
FIG. 6 shows a first type of 2D views displayed on the user interface for guiding the positioning of the robotic device relative to the target axis, according to an embodiment of the invention.

FIG. 6 shows a first type of 2D views displayed on the screen of the user interface for guiding the positioning of the robotic device relative to the target axis, according to an embodiment of the invention (top) and corresponding side views of the working space relative to a vertebra and the target axis (bottom), in three situations.

In this embodiment, the pose of the guiding device is represented by two circles: a first circle C1 having a center representing the center of a distal section of the guiding device 303; a second circle C2 having a center representing the center of a proximal section of the guiding device 303.

The plane of the screen corresponds to a plane perpendicular to the target axis T. The centers of the circles C1, C2 are computed as the orthogonal projections of the centers of the distal and proximal sections of the guiding device onto said plane.

A cross C is also displayed on the screen. The intersection point of the cross is computed as the intersection between the target axis T and the above-mentioned plane.

The relative position of the circles C1, C2 relative to the cross C indicates the distance between the guiding axis and the target axis.

In order to align the guiding the guiding axis with the target axis, the goal of the user is thus to make the centers of the circles coincide with the cross. This representation is standard in navigation systems and it is usually difficult to perform manually.

When the user moves the robotic device during the approach step, the user interface displays in real time the corresponding displacement of the circles relative to the cross.

In addition, the user interface also displays information relating to the working space of the robotic device.

In the situation represented at the left of the figure, the guiding device 303 is not aligned with the target axis, the latter passing through a pedicle of a vertebra V. This is represented, on the screen of the user interface, by the fact that the circles C1, C2 are distant from each other and in particular by the fact that their centers do not coincide with the intersection point of the cross C.

Besides, the working space W of the robotic device does not allow achieving said alignment. This is represented, on the screen of the user interface, by a specific color and thickness of the contour (in the illustrated embodiment, a thin dark square I). Of course, instead of the contour, any other element having at least one feature variable as a function a distance between the envelope of the working space and the target axis could be used as an indicator.

In the situation represented in the middle of the figure, the guiding device 303 is aligned with the target axis T. This is represented, on the screen of the user interface, by the fact that the circles substantially overlap, with their centers substantially coinciding with the intersection point of the cross.

However, the working space W is not centered on the target axis T, which is not desirable since there may not been enough margin in case of a further relative movement of the patient relative to the guiding device. This is represented, on the screen of the user interface, by a specific color and thickness of the contour, different from the previous situation (in the illustrated embodiment, a thicker square I, with the same dark color).

In the situation represented at the right of the figure, the guiding device 303 is still aligned with the target axis T. This is still represented, on the screen of the user interface, by the fact that the circles C1, C2 substantially overlap, with their centers substantially coinciding with the intersection point of the cross C.

In this situation, the working space W is substantially centered on the target axis T, which is a suitable configuration. This is represented, on the screen of the user interface, by a specific color and thickness of the contour, different from the previous situation (in the illustrated embodiment, a thicker square I, with a light color).

Figure 7:
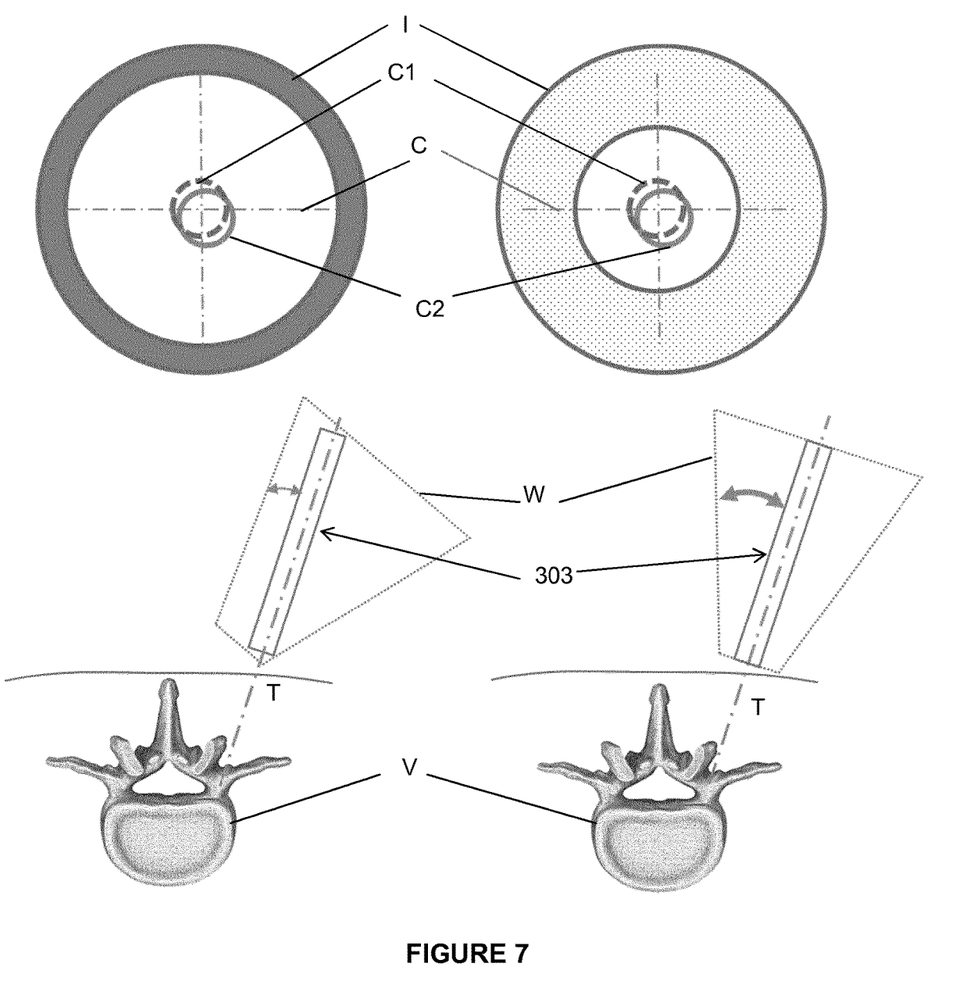
FIG. 7 shows a second type of 2D views displayed on the user interface for guiding the positioning of the robotic device relative to the target axis, according to another embodiment of the invention.

FIG. 7 shows a second type of 2D views displayed on the screen of the user interface for guiding the positioning of the guiding axis relative to the target axis, according to another embodiment of the invention (top), and corresponding side views of the working space relative to a vertebra and the target axis (bottom), in two situations.

In this embodiment, the pose of the guiding device is represented by two circles C1, C2 relative to a cross C representing the target axis as in FIG. 6. The circles and cross will thus not be described again.

In the embodiment of FIG. 7, the compensation margin, which indicates a distance between the target axis T and the envelope of the working space W of the robotic device, is represented as a crown I of variable width: a large width corresponding to a large compensation margin, a small width corresponding to a small compensation margin. During variation of the crown width, the external diameter of the crown may remain the same, only the internal diameter varying.

The crown may also be colored and/or textured in a variable way depending on the compensation margin. For example, the crown may be orange when the compensation margin is small, and green when the compensation margin is large.

In order to align the guiding the guiding axis 303 with the target axis T, the goal of the user is thus to make the centers of the circles coincide with the cross.

When the user moves the robotic device, the user interface displays in real time the corresponding displacement of the circles relative to the cross, along with the variation of the crown width depending on the variation of the compensation margin.

In the situation represented on the left of the figure, the guiding device 303 is aligned with the target axis T. This is represented, on the screen of the user interface, by the fact that the circles C1, C2 substantially overlap, with their centers substantially coinciding with the intersection point of the cross C. However, the working space W is not centered relative to the target axis T, which implies that the compensation margin is small. This is represented by a crown having a dark color and a relatively small width.

In the situation represented on the right of the figure, the guiding device 303 is aligned with the target axis T. This is represented, on the screen of the user interface, by the fact that the circles substantially overlap, with their centers substantially coinciding with the intersection point of the cross, as on the left part of the figure. However, in this case, the working space W is substantially centered relative to target axis T, which implies that the compensation margin is larger than in the left part of the figure. This is represented by a crown having a light color and a relatively large width.

Figure 8:
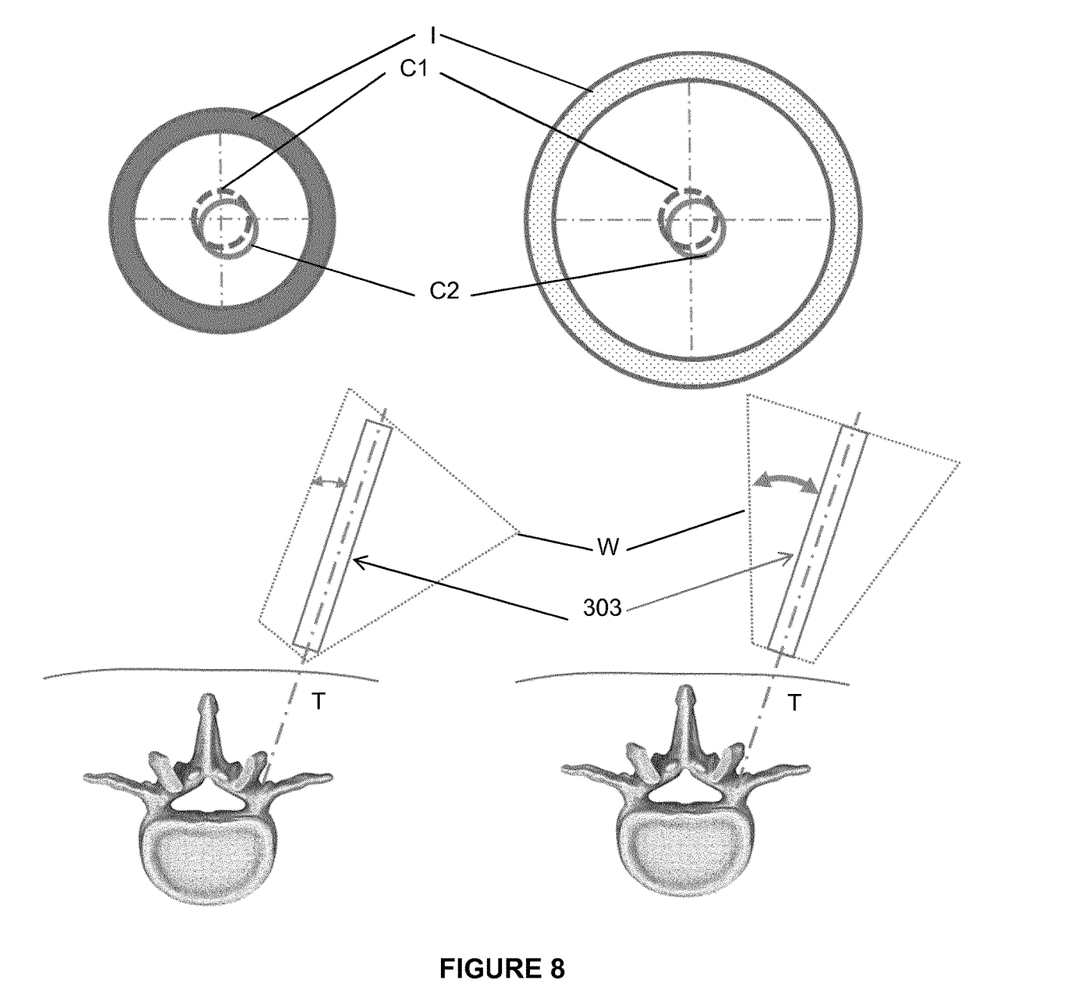
FIG. 8 shows a third type of 2D views displayed on the user interface for guiding the positioning of the robotic device relative to the target axis, according to another embodiment of the invention.

FIG. 8 shows a third type of 2D views displayed on the screen of the user interface for guiding the positioning of the guiding axis relative to the target axis, according to another embodiment of the invention (top), and corresponding side views of the working space of the robotic device relative to a vertebra and the target axis (bottom), in two situations.

The circles C1, C2, cross C and crown represent the same information as in FIG. 7 and will thus not be described in detail again.

In this embodiment, the crown I representing the compensation margin has a constant width, but variable external and internal diameters. The external diameter of the crown increases as the compensation margin increases.

The crown may also be colored and/or textured in a variable way depending on the compensation margin. For example, the crown may be orange when the compensation margin is small and green when the compensation margin is large.

In the situation represented on the left of the figure, the guiding device 303 is aligned with the target axis T. This is represented, on the screen of the user interface, by the fact that the circles C1, C2 substantially overlap, with their centers substantially coinciding with the intersection point of the cross. However, the working space W is not centered relative to the target axis T, which implies that the compensation margin is small. This is represented by a crown having a dark color and a relatively small external diameter.

In the situation represented on the right of the figure, the guiding device 303 is aligned with the target axis T. This is represented, on the screen of the user interface, by the fact that the circles substantially overlap, with their centers substantially coinciding with the intersection point of the cross, as on the left part of the figure. However, in this case, the working space W is substantially centered relative to the target axis T, which implies that the compensation margin is larger than in the left part of the figure. This is represented by a crown having a light color and a relatively large external diameter.

Instead of 2D views as shown in FIGS. 6-8, the user interface may display 3D views.

Figure 9A:
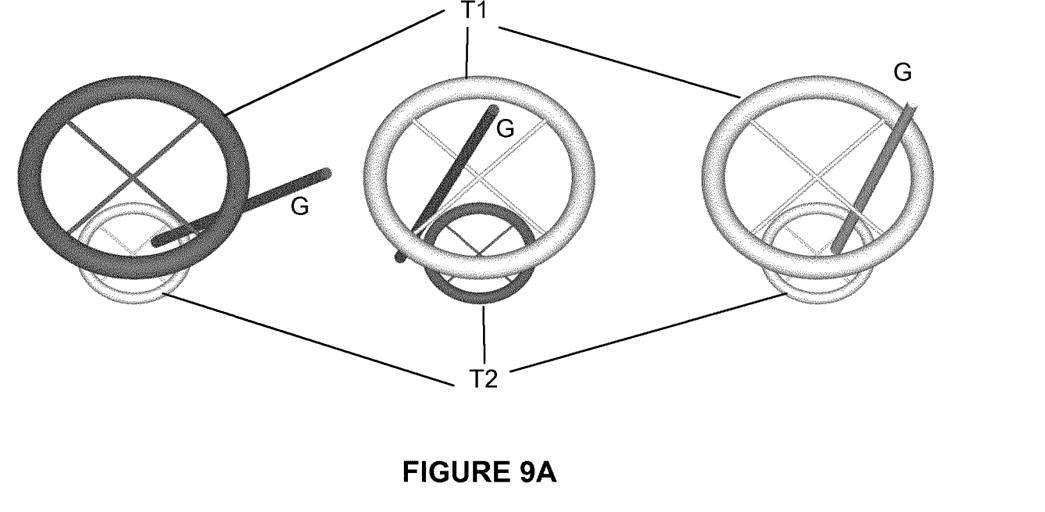
FIGS. 9A-9B show a first type of 3D views displayed on the user interface for guiding the positioning of the robotic device relative to the target axis, according to an embodiment of the invention.
Figure 9B:
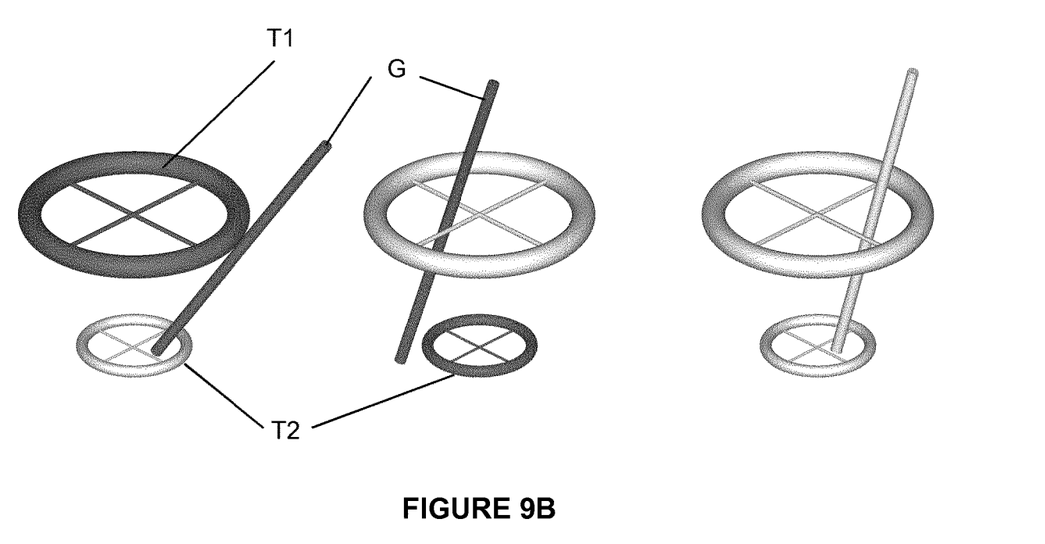

FIGS. 9A-9B show a first type of 3D views displayed on the screen of the user interface for guiding the positioning of the robotic device relative to the target axis, according to an embodiment of the invention.

A first torus T1 represents a distal section of the envelope of the working space; a second torus T2 represents the proximal section of the envelope of the working space. The intersection between the target axis and the plane of each torus is represented by a respective cross. A bar represents the guiding axis G.

Advantageously, the tori and bar are represented from a point of view which substantially corresponds to the position of the user relative to the vertebra. Thus, the representation of the position of the robotic device relative to the target axis is more intuitive for the user. This consistent orientation can be predefined for a given set up of the user, the patient and the display since it is usually a constant setup. The 3D view can also be moved to match the viewpoint of the user.

For example, in FIG. 9A, the tori and bar are viewed from an angle of about 30°.

In FIG. 9B, the tori and bar are viewed from an angle of about 60°.

The goal of the user is to place the bar within both tori, as close as possible to the centers of the tori.

To help this positioning, the color and/or texture of the tori may change.

For example, at the left of FIGS. 9A and 9B, the bar is inside the proximal torus T2, which may be displayed in green color (represented by a light color) but outside the distal torus T1, which may be displayed in orange (represented by a dark color). The bar is also in a dark color, showing that the guiding device cannot be aligned with the target axis.

At the middle of FIGS. 9A and 9B, the bar is outside the proximal torus T2, which may be displayed in orange color (represented by a dark color) but inside the distal torus T1, which may be displayed in green (represented by a light color). The bar is also in a dark color, showing that the guiding device cannot be aligned with the target axis.

At the right of FIGS. 9A and 9B, the bar is inside both tori T1, T2, which are thus displayed in the same light color. The bar is also in a light color, showing that the guiding device can be aligned with the target axis using the actuation device.

Figure 10:
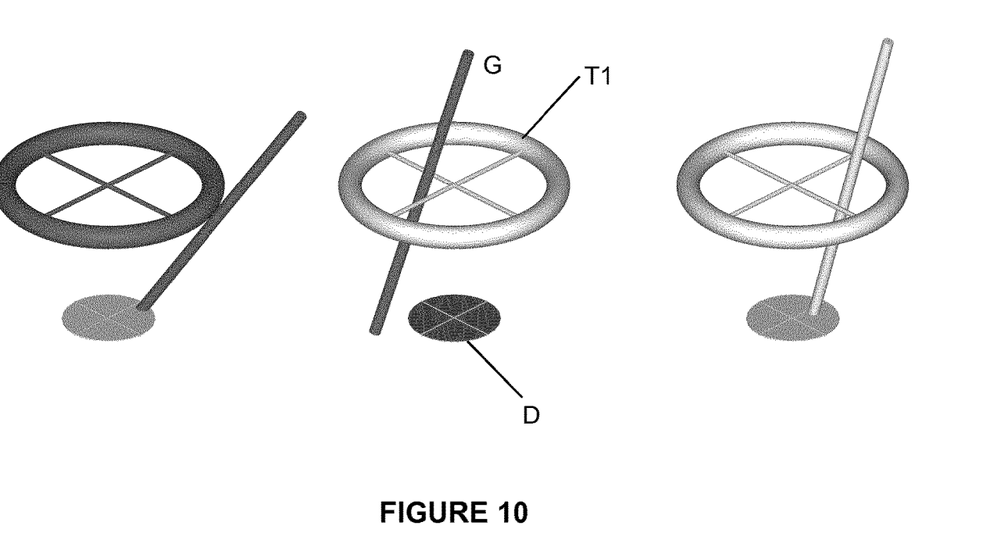
FIG. 10 shows a second type of 3D views displayed on the user interface for guiding the positioning of the robotic device relative to the target axis, according to another embodiment of the invention.

FIG. 10 shows a second type of 3D view displayed on the screen of the user interface for guiding the positioning of the guiding axis relative to the target axis, according to another embodiment of the invention.

As compared to the view of FIG. 9B, the proximal torus T2 is replaced by a disc D.

Apart from this, the implementation of the user interface is similar to the one already described for FIG. 9B.

This disc represents a flat surface which may be either the patient's skin, the entry point in the vertebra (in particular in case of open surgery), or a target point within the vertebra (e.g. the center of the pedicle). In the latter case, the disc may contain a slice of the 3D medical image that was used for the planning, passing through the target point.

Of course, the skilled person may select any other representation (in terms of shape, color, texture, etc.) of the pose of the working space relative to the target axis, in particular to take into account ergonomics and intuitiveness required by the user.

The system according to the invention can be used for other parts of the body, with fixed bones or articulated bones, for example on the knee, the hip, the shoulder, the skull, each time it is necessary to perform a linear trajectory of a surgical tool.

REFERENCES

EP1414362

The invention claimed is:

1. A robotic-assisted surgical system, comprising:
   a robotic device for constraining a surgical tool to a guiding axis and adjusting a pose of the guiding axis, wherein a portion of the robotic device is configured to contact a patient; and
   a control unit configured to:
      compare the pose of the guiding axis with a planned target axis;
      determine a working space of the robotic device; and
      cause a display device to display:
         a representation of the target axis;
         a representation of the guiding axis, wherein an overlap of the representation of the guiding axis with the representation of the target axis is indicative that the axes are aligned; and
         a representation of a distance between the target axis and an envelope of the working space, wherein, if the distance between the target axis and the envelope of the working space is below a predetermined threshold, the representation is displayed as a first color, diameter, or thickness, and, if the distance between the target axis and the envelope of the working space is above the predetermined threshold, the representation is displayed as a second color, diameter, or thickness.

2. The system of claim 1, wherein the representation of the distance between the target axis and the envelope of the working space is displayed as having at least two of a color, a diameter, or a thickness differing depending on whether the distance is above or below the predetermined threshold.

3. The system of claim 1, wherein the control unit is configured to cause the display device to display 2D representations of the target axis and the guiding axis.

4. The system of claim 3, wherein the representation of the target axis is a cross.

5. The system of claim 3, wherein the representation of the guiding axis comprises a first circle representing a distal point of the guiding axis and a second circle representing a proximal point of the guiding axis.

6. The system of claim 3, wherein the representation of the distance between the target axis and the envelope of the working space is a circle.

7. The system of claim 3, wherein the representation of the distance between the target axis and the envelope of the working space is a rectangle.

8. The system of claim 1, wherein the portion of the robotic device configured to contact the patient is a support unit.

9. The system of claim 8, wherein the support unit is connected to a base and configured to contact the patient to provide a partial mechanical link between the robotic device and the patient.

10. The system of claim 7, wherein the robotic device further comprises an actuation unit movable relative to a base for adjusting the pose of the guiding axis with respect to the target axis.

11. The system of claim 10, further comprising a passive articulated lockable holding arm supporting the base of the robotic device.

12. The system of claim 11, wherein the actuation unit is configured to be activated only when the holding arm is locked.

13. The system of claim 11, wherein the robotic device further comprises a trigger configured to simultaneously lock the holding arm and activate the actuation unit to adjust the pose of the guiding axis.

14. A robotic-assisted surgical system, comprising:
   a robotic device for constraining a surgical tool to a guiding axis and adjusting a pose of the guiding axis, wherein a portion of the robotic device is configured to contact a patient; and
   a control unit configured to:
      compare the pose of the guiding axis with a planned target axis;
      determine a working space of the robotic device; and
      cause a display device to display:

a representation of the target axis;
a representation of the guiding axis;
a representation of a distal section of an envelope of the working space; and
a representation of a proximal section of the envelope of the working space, wherein:
if the guiding axis is aligned in both sections of the working space, the representations of the distal section and the proximal section are displayed in a same color; and
if the guiding axis is not aligned in both sections of the working space, the representations of the distal section and the proximal section are displayed in different colors.

15. The system of claim 14, wherein the control unit is configured to cause the display device to display 3D representations of the target axis and the guiding axis.

16. The system of claim 15, wherein the representation of the target axis is a first cross having an intersection representing a distal point of the target axis and a second cross having an intersection representing a proximal point of the target axis.

17. The system of claim 15, wherein the representation of the guiding axis comprises a bar.

18. The system of claim 14, wherein the control unit is configured to cause the display device to display the representation of the distal section of the envelope of the working space as a torus.

19. The system of claim 18, wherein the control unit is configured to cause the display device to display the representation of the proximal section of the envelope of the working space as a torus.

20. The system of claim 18, wherein the control unit is configured to cause the display device to display the representation of the proximal section of the envelope of the working space as a disc representing a reference surface.

* * * * *